US00PP15203P2

(12) United States Plant Patent
Crowder

(10) Patent No.: US PP15,203 P2
(45) Date of Patent: Oct. 5, 2004

(54) ***ABELIA* PLANT NAMED 'MARDI GRAS'**

(50) Latin Name: *Abelia grandiflora×chinensis*
Varietal Denomination: Mardi Gras

(76) Inventor: Rick Crowder, P.O. Box 3349, Hickory, NC (US) 28603

( * ) Notice: Subject to any disclaimer, the term of this patent is extended or adjusted under 35 U.S.C. 154(b) by 0 days.

(21) Appl. No.: 10/746,651

(22) Filed: Dec. 29, 2003

(51) Int. Cl.[7] ..... A01H 5/00
(52) U.S. Cl. ..... Plt./226
(58) Field of Search ..... Plt./226

*Primary Examiner*—Kent Bell

(57) ABSTRACT

A new cultivar of *Abelia* named 'Mardi Gras' that is characterized by green and white variegated foliage with pink coloring on the young leaves, compact low-growing habit and pink-white flowers. In combination these traits set 'Mardi Gras' apart from all other existing varieties of *Abelia* known to the inventor.

1 Drawing Sheet

Genus, species: *Abelia grandiflora×chinensis.*
Varietal denomination: 'Mardi Gras'.

BACKGROUND OF THE INVENTION

The present invention relates to a new and distinct cultivar of *Abelia* grown as an ornamental for use in the landscape. The new cultivar is known botanically as *Abelia grandiflora×chinensis* and will be referred to hereinafter by the cultivar name 'Mardi Gras'.

'Mardi Gras' was discovered as a naturally occurring branch sport on an individual *Abelia grandiflora×chinensis* found in a crop of *Abelia grandiflora×chinensis.* The inventor discovered the sport in a cultivated area of North Carolina in the United States. 'Mardi Gras' was selected for its green, white and pink variegated foliage. The crop of *Abelia grandiflora×chinensis* was part of a breeding program designed to cross hybridize *Abelia grandiflora* and *Abelia chinensis.* The parent of 'Mardi Gras' is *Abelia grandiflora×Abelia chinensis* #9 (unpatented), and exhibits green foliage. 'Mardi Gras' is distinguishable from the parent by pronounced variegated foliage.

'Mardi Gras' is a compact, low-growing shrub with variegated foliage that exhibits pink coloring on the young leaves, pink-white flowers, and red-bronze stems. The traits that characterize 'Mardi Gras' as a distinct and unique variety are variegated foliage, compact form, and low-growing habit.

The two closest comparison plants are *Abelia* 'Sunrise' (U.S. Plant Pat. No. 9,698) and *Abelia* 'Conti' (U.S. Plant Pat. No. 8,472). 'Mardi Gras' is distinguishable from the comparison plants by slightly larger leaves, pronounced variegation of the leaves, and prominent pink coloring of the young leaves. It is the first and only variegated form of *Abelia grandiflora×chinensis* cross known to the inventor.

'Mardi Gras' was first asexually propagated by the inventor in North Carolina in 2000. Asexual propagation was accomplished using softwood cuttings. Since that time, under careful observation, the distinguishing characteristics have been determined stable and uniform in successive generations. The new plant reproduces true to type through successive generations of asexual reproduction.

SUMMARY OF THE INVENTION

The following represent the distinguishing characteristics of the new *Abelia* cultivar 'Mardi Gras'. In combination these traits set 'Mardi Gras' apart from all other existing varieties of *Abelia* known to the inventor. 'Mardi Gras' has not been tested under all possible conditions and phenotypic differences may be observed with variations in environmental, climatic, and cultural conditions, however, without any variance in genotype.

1. *Abelia* 'Mardi Gras' exhibits pronounced green and white variegated foliage, and additional pink coloring of the young leaves.
2. *Abelia* 'Mardi Gras' is 60–75 cm. in height and 120–150 cm. in width at maturity.
3. *Abelia* 'Mardi Gras' exhibits pink-white flowers.
4. *Abelia* 'Mardi Gras' exhibits a compact low-growing habit.
5. *Abelia* 'Mardi Gras' is suitable for use as a foundation plant or for mass planting in the landscape.
6. *Abelia* 'Mardi Gras' performs well in loam and clay soils.

BRIEF DESCRIPTION OF THE DRAWING

The accompanying color drawing illustrates the overall appearance of the new *Abelia* cultivar 'Mardi Gras' showing the colors as true as it is reasonably possible to obtain in colored reproductions of this type. Colors in the photograph may differ from the color values cited in the detailed botanical description, which accurately describe the actual colors of the new variety 'Mardi Gras'. The plant in the photograph is a 2-liter container that is 18-months-old and was grown in full sun out-of-doors in Arroyo Grande, Calif.

The drawing on sheet 1 illustrates the entire plant.

The photograph was taken using conventional techniques and although foliage colors may appear different from actual colors due to light reflectance, they are as accurate as possible by conventional photography.

BOTANICAL DESCRIPTION OF THE PLANT

The following is a detailed description of the *Abelia* cultivar named 'Mardi Gras'. Data was collected in Arroyo Grande, Calif. from plants grown in 2-liter containers out-of-doors in full sun. The plants were approximately 18-months-old at the time. Color determinations are in accordance with The Royal Horticultural Society Colour Chart except where general color terms of ordinary dictionary significance are used. 'Mardi Gras' has not been tested under all possible conditions and phenotypic differences may be observed with variations in environmental, climatic, and cultural conditions, however, without any variance in genotype. The growing requirements are similar to the species. Under normal growing conditions there are no known disease problems known to the inventor.

Botanical classification: *Abelia* 'Mardi Gras'.
Species: *grandiflora×chinensis*.
Uses: Ornamental landscape plant.
Parent: 'Mardi Gras' is a branch sport from the parent plant *Abelia grandiflora×chinensis* #9.
Type: Shrub.
Vigor: Medium vigor.
Habit: Compact and low-growing.
Form: Spreading mound.
Height: 60–75 cm. in height at maturity.
Width: 120–150 cm. in width at maturity.
Hardiness: USDA Zones 6–9.
Propagation: Softwood cuttings.
Root system: Fine and fibrous.
Soil: Plant in loam or clay soil.
Sunlight: Plant in full sunlight.
Time to initiate roots: 6–8 weeks are required at air temperature of 21–32° Centigrade for an initial cutting to produce roots.
Crop time: 18–24 months are required to produce a finished 2-liter container from a rooted cutting.
Seasonal interest: Pink-white flowers in summer.
Diseases and pests: None known to inventor.
Stems:
- *Branching habit.*—Divergent.
- *Internode length.*—1.50 cm. between nodes.
- *Stem diameter.*—1 mm. in diameter.
- *Stem length.*—27 cm. in length.
- *Shape.*—Cylindrical.
- *Surface.*—Pubescent.
- *Stem color.*—182A.

Foliage:
- *Leaf arrangement.*—Opposite.
- *Leaf division.*—Simple.
- *Leaf shape* (*young and mature*).—Ovate.
- *Leaf base* (*young and mature*).—Rounded.
- *Leaf apex* (*young leaves*).—Acute.
- *Leaf apex* (*mature leaves*).—Apiculate.
- *Leaf venation.*—Pinnate.
- *Vein color for young and mature leaves* (*adaxial surface*).—158A.
- *Vein color for young and mature leaves* (*abaxial surface*).—158A.
- *Stipules.*—Present.
- *Stipule dimensions.*—2 mm. in length and 1 mm. in width.
- *Stipule surface.*—Pubescent.
- *Stipule color.*—182A.
- *Young leaf surface* (*adaxial*).—Puberulent.
- *Young leaf surface* (*abaxial*).—Puberulent.
- *Mature leaf surface* (*adaxial*).—Few hairs.
- *Mature leaf surface* (*abaxial*).—Few hairs.
- *Leaf attachment.*—Petiolate.
- *Petiole dimensions.*—3 mm. in length and 1 mm. in diameter.
- *Petiole color.*—Both colors 182A and 138C are present on each individual petiole.
- *Petiole shape.*—Sulcate.
- *Petiole surface.*—Puberulent.
- *Leaf margin* (*young and mature*).—Serrulate.
- *Leaf appearance* (*young*).—Dull.
- *Leaf appearance* (*mature*).—Glossy.
- *Mature leaf dimensions.*—2.75 cm. in length and 1.50 cm. in width.
- *Young leaf dimensions.*—1.50 cm. in length and 0.75 cm. in width.
- *Mature leaf color* (*adaxial surface*).—Colors 147A and 158A are both individually present on an individual leaf.
- *Mature leaf color* (*abaxial surface*).—Colors 147B and 158B are both individually present on an individual leaf.
- *Young leaf color* (*adaxial surface*).—Colors 147A, 158A and 181C are all individually present on an individual young leaf.
- *Young leaf color* (*abaxial surface*).—Colors 147A, 158A and 181C are all individually present on an individual young leaf.
- *Foliar fragrance.*—None observed.

Flower:
- *Inflorescence.*—Cyme.
- *Inflorescence dimensions.*—6 cm. in length and 6 cm. in width.
- *Quantity of flowers.*—A range of 30–35 flowers per cyme.
- *Persistent or self-cleaning.*—Self-cleaning.
- *Color of peduncle.*—165B.
- *Peduncle length.*—10 cm. in length.
- *Peduncle diameter.*—2 mm. in diameter.
- *Surface of peduncle.*—Puberulent.
- *Pedicel color.*—182A.
- *Pedicel dimensions.*—6 mm. in length and 1 mm. in width.
- *Shape of flower.*—Tubular.
- *Aspect.*—Facing upwards.
- *Bud shape.*—Club-shaped.
- *Bud color.*—70C.
- *Bud surface.*—Puberulent.
- *Bud dimensions.*—11 mm. in length and 4 mm. in diameter.
- *Flower dimensions.*—2 cm. in length and 1 cm. in width.
- *Corolla tube depth.*—12 mm. in depth.
- *Corolla tube color.*—60C.
- *Petals.*—Five in number.
- *Color of petals.*—69C.
- *Shape of petal.*—Elongated.
- *Fused or unfused.*—Petals are fused.
- *Dimensions of petal.*—2 cm. in length and 2 mm. in width.
- *Calyx shape.*—Tubular.
- *Calyx dimensions.*—4 mm. in width and 2 mm. in length.
- *Color of calyx.*—191A.
- *Surface of calyx.*—Puberulent.
- *Sepals.*—Five in number.
- *Blooming period.*—Spring and summer.
- *Fragrance.*—Sweet fragrance.

Reproduction organs:

*Stamens.*—Four attached to corolla tube at base.

*Stamen shape.*—Filament.

*Dimensions of stamen.*—15 mm. in length and less 0.50 mm. in width.

*Color of stamen filament.*—155A.

*Dimensions of anther.*—0.25 mm. in width and 1 mm. in length.

*Pollen color.*—187D.

*Amount of pollen.*—Small amount.

*Anther color.*—187D.

*Pistil.*—One.

*Color of pistil.*—155A.

*Pistil shape.*—Club-shaped.

*Dimensions of pistil.*—15 mm. in length and less than 0.50 mm. in diameter.

*Ovary position.*—Inferior.

*Ovary color.*—191A.

*Ovary shape.*—Oblong.

*Ovary dimensions.*—2 mm. in diameter and 6 mm. in length.

Seed: No seed has been observed to date.

I claim:

1. A new and distinct variety of *Abelia* plant named 'Mardi Gras' as described and illustrated.

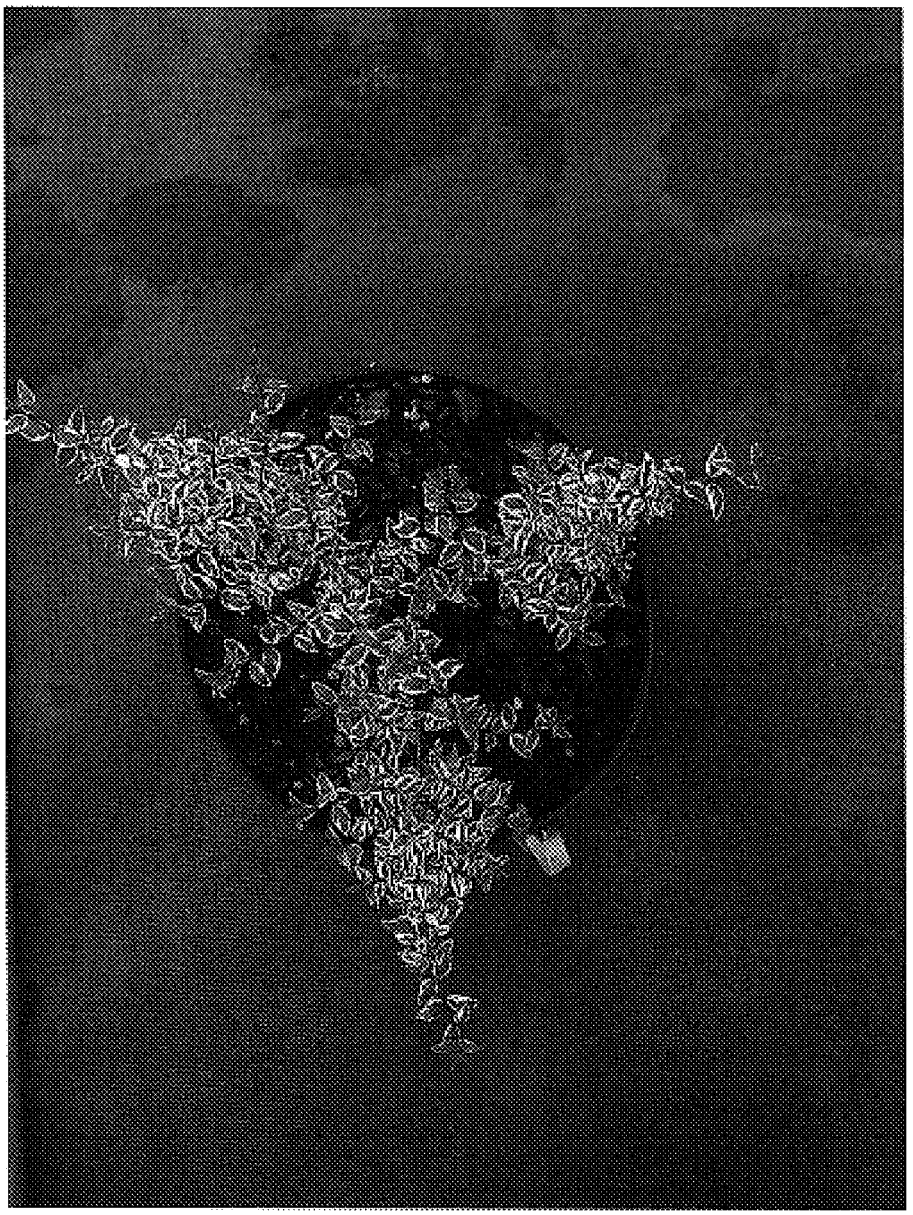

* * * * *